United States Patent
Lin et al.

(10) Patent No.: US 10,429,328 B2
(45) Date of Patent: *Oct. 1, 2019

(54) MEMS-BASED ISOTHERMAL TITRATION CALORIMETRY

(71) Applicant: The Trustees of Columbia University in the City of New York, New York, NY (US)

(72) Inventors: Qiao Lin, New York, NY (US); Bin Wang, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 525 days.

This patent is subject to a terminal disclaimer.

(21) Appl. No.: 14/603,848

(22) Filed: Jan. 23, 2015

(65) Prior Publication Data

US 2015/0285751 A1 Oct. 8, 2015

Related U.S. Application Data

(63) Continuation of application No. PCT/US2013/051910, filed on Jul. 24, 2013.

(Continued)

(51) Int. Cl.
*G01K 17/00* (2006.01)
*G01N 25/48* (2006.01)
(Continued)

(52) U.S. Cl.
CPC ...... *G01N 25/482* (2013.01); *B01L 3/502715* (2013.01); *B01L 7/00* (2013.01);
(Continued)

(58) Field of Classification Search
CPC combination set(s) only.
See application file for complete search history.

(56) References Cited

U.S. PATENT DOCUMENTS 3,071,495 A 1/1963 Hanlein
3,552,207 A 1/1971 Monk et al.
(Continued)

FOREIGN PATENT DOCUMENTS

JP SHO51-101378 7/1976
JP 2001-165881 6/2001
(Continued)

OTHER PUBLICATIONS

U.S. Appl. No. 13/972,783, Feb. 25, 2016 Final Office Action.
(Continued)

*Primary Examiner* — Lisa Caputo
*Assistant Examiner* — Nasir U Ahmed
(74) *Attorney, Agent, or Firm* — Baker Botts L.L.P.

(57) ABSTRACT

A microelectromechanical systems-based calorimetric device includes first and second micromixers and first and second thermally-isolated microchambers. A first solution including a sample and a reagent is introduced to the first microchamber via the first micromixer, and a second solution including a sample and a buffer is introduced to the second microchamber via the second micromixer. A thermopile measures the differential temperature between the first microchamber and the second microchamber and outputs a voltage representative of the difference. The output voltage can be used to calculate reaction parameters.

20 Claims, 15 Drawing Sheets

Related U.S. Application Data

(60) Provisional application No. 61/675,025, filed on Jul. 24, 2012, provisional application No. 61/769,591, filed on Feb. 26, 2013.

(51) Int. Cl.
   *B01L 3/00* (2006.01)
   *B01L 7/00* (2006.01)

(52) U.S. Cl.
   CPC ......... *G01K 17/00* (2013.01); *G01N 25/4893* (2013.01); *B01L 2200/027* (2013.01); *B01L 2200/14* (2013.01); *B01L 2300/0663* (2013.01); *B01L 2300/0877* (2013.01); *B01L 2300/0883* (2013.01); *B01L 2300/1827* (2013.01)

(56) References Cited

U.S. PATENT DOCUMENTS

| | | | |
|---|---|---|---|
| 4,040,288 | A | 8/1977 | Kotelnikov et al. |
| 4,333,332 | A | 6/1982 | Privalov |
| 5,439,291 | A | 8/1995 | Reading |
| 5,813,763 | A | 9/1998 | Plotnikov et al. |
| 6,079,873 | A | 6/2000 | Cavicchi et al. |
| 6,185,232 | B1 | 2/2001 | Hess, Jr. et al. |
| 6,561,692 | B2 | 5/2003 | Danley |
| 6,988,826 | B2 | 6/2006 | Zibri et al. |
| 7,564,267 | B1 | 7/2009 | Patterson |
| 7,578,613 | B2 | 8/2009 | Reading |
| 7,794,136 | B2 | 9/2010 | Yang et al. |
| 8,577,658 | B2 * | 11/2013 | Howell, Jr. ......... G06F 17/5018 703/2 |
| 2002/0115200 | A1 | 8/2002 | Zou et al. |
| 2002/0121136 | A1 | 9/2002 | Rudent et al. |
| 2003/0072348 | A1 | 4/2003 | Danley |
| 2003/0106799 | A1 | 6/2003 | Covington et al. |
| 2003/0225360 | A1 | 12/2003 | Eppstein et al. |
| 2004/0038426 | A1 | 2/2004 | Manalis |
| 2004/0180204 | A1 | 9/2004 | Zumbrunnen et al. |
| 2005/0254547 | A1 | 11/2005 | Zribi et al. |
| 2006/0187998 | A1 | 8/2006 | Danley |
| 2007/0148416 | A1 | 6/2007 | Wolkin et al. |
| 2007/0286769 | A1 | 12/2007 | Vlassak et al. |
| 2011/0216804 | A1 | 9/2011 | Roukes et al. |
| 2011/0286493 | A1 | 11/2011 | Torniainen et al. |
| 2013/0255361 | A1 | 10/2013 | Juncker et al. |
| 2016/0216163 | A1 | 7/2016 | Lin et al. |

FOREIGN PATENT DOCUMENTS

| | | |
|---|---|---|
| JP | 2001-349855 | 12/2001 |
| JP | 2012-51762 A | 3/2012 |
| WO | WO 1998/016818 | 4/1998 |
| WO | WO 2009/059110 A1 | 5/2009 |
| WO | WO 2011/142518 A1 | 11/2011 |
| WO | 2012/116092 | 8/2012 |
| WO | WO 2012/116092 | 8/2012 |
| WO | WO 2014/018688 | 1/2014 |
| WO | WO 2014/197740 A1 | 12/2014 |

OTHER PUBLICATIONS

U.S. Appl. No. 13/972,783, Dec. 16, 2015 Response to Non-Final Office Action.
U.S. Appl. No. 13/972,783, Aug. 2, 2016 Notice of Allowance.
U.S. Appl. No. 13/972,783, Jul. 1, 2016 Applicant Initiated Interview Summary.
U.S. Appl. No. 13/972,783, Jun. 27, 2016 Amendment and Request for Continued Examination (RCE).
Supplementary European Search Report dated Jun. 21, 2016 in EP Application No. 13822418.
Supplementary European Search Report dated Apr. 15, 2016 in EP Application No. 12748936.
U.S. Appl. No. 13/972,783 (US 2014/0092935), filed Aug. 21, 2013 (Apr. 3, 2014)
Allen, et al., "MEMS-Based Scanning Calorimeter for Thermodynamic Properties of Nanostructures", *Microscale Thermaphysical Engineering*, 2:11-19 (1998).
Barnes et al., "A femtojoule calorimeter using micromechanical sensors", *AIP: Review of Scientific Instruments*, 65:3793-3798 (Dec. 1994).
Carpentier, et al., "Temperature-Modulated Differential Scanning Calorimetry as a Specific Heat Spectroscopy", *Journal of Physics D: Applied Physics*, 35(4): 402-408 (2002).
Cavicchi et al., "Micro-differential scanning calorimeter for combustible gas sensing", *Sensors and Actuators B; Chemical*, 97(1):22-30 (Jan. 2004).
Craig, et al., "The Use of Modulated Temperature DSC for the Study of Pharmaceutical Systems: Potential Uses and Limitations", *Pharmaceutical Research*, 15(8):1152-1153 (1998).
Feire, "Differential Scanning Calorimetry", *Methods in Molecular Biology*, 40:191-218 (1995).
Finotello, et al., "AC Calorimetric Studies of Phase Transitions in Porous Substrates. Superfluid Helium and Liquid Crystals", *Thermochimica Acta*, 304-305:303-316 (1997).
Garden, et al., "Entropy Production in AC-Calorimetry", *Thermochimica Acta*, 461(1-2):57-66 (2007).
GE Healthcare Life Sciences, "MicroCal" http://www.gelifesciences.com/webapp/wcs/stores/servlet/catalog/en/GELifeSciences-uk/brands/microcal/# [Retrieved on Dec. 17, 2013].
Gill, "Modulated Differential Scanning Calorimetry", *Journal of Thermal Analysis*, 40:931-939 (1993).
Gill, et al., Differential Scanning Calorimetry Techniques: Applications in Biology and Nanoscience:, *Journal of Biomolecular Techniques*, 21(4):167-193 (Dec. 2010) [retrieved Jun. 21, 2011].
Hinz, et al., "Measurement and Analysis of Results Obtained on Biological Substances with D.S.C.", *Journal of Chemical Thermodynamics*, 33:1511-1525 (2001).
Höhne, et al., "Differential Scanning Calorimetry", Springer, Table of Contents (2003).
Huth, et al., "Differential AC—Chip Calorimeter for Glass Transition Measurements in Ultrathin Films", *Journal of Polymer Science Part B: Polymer Physics*, 44(20):2996-3005 (Oct. 2006).
Inoue, et al., "AC-Calorimetry for Detecting Electronic Phase Transitions at Low Temperatures using Micro-Chip Devices", *Thermochimica Acta*, 492(1):85-88 (2009).
International Search Report and Written Opinion for PCT/US2012/026163, dated Jun. 29, 2012).
International Search Report and Written Opinion for PCT/US2014/041181,dated Oct. 9, 2014.
International Search Report dated Dec. 11, 2013 in PCT/US13/51910.
Jung, et al., "Peltier AC Calorimeter", *Thermochimica Acta*, 391:7-12 (2002).
Lai et al., "High-speed (104 °C/s) scanning microcalorimetry with monolayer sensitivity ($J/m^2$)", *Applied Physics Letters*, 67:1229-1231 (Aug. 1995).
Lee, et al., "High-Sensitivity Microfluidic Calorimeters for Biological and Chemical Applications", *PNAS*, 106(36): 15225-15230 (Sep. 2009).
Lerchner, et al., "Chip Calorimetry and Its Use for Biochemical and Cell Biological Investigations", *Chemical Engineering and Processing*, 47:991-999 (2008).
Lortz, et al., "Modulated-Bath AC Calorimetry Using Modified Commercial Peltier-Elements", *Review of Scientific Instruments*, 76:103902 (20 pages) (2005).
Maggiolino, et al., "MEMS_DSC: A New Device for Microcalorimetric Analysis in the Biological Field", *Microsystems Technologies*, 16(6): 967-971 (Jun. 2010).
Olson, et al., "The Design and Operation of a MEMS Differential Scanning Nanocalorimeter for High-Speed Heat Capacity Measurements of Ultrathin Films", *Journal of Microelectromechanical Systems*, 12(3):355-364 (Jun. 2003).

(56) References Cited

OTHER PUBLICATIONS

Plotnikov, et al., "A New Ultrasensitive Scanning Calorimeter", *Analytical Biochemistry*, 250(2):237-244 (1997).
Robertson, et al., "Protein Structure and the Energetics of Protein Stability", *Chemical Reviews*, 97:1251-1267 (1997).
Rowe, D.M., "CRC Handbook of Thermoelectrics", 1st Ed.: CRC-Press, Boca Raton, FL, Table of Contents (1995).
van Herwaarden, et al., "Overview of Calorimeter Chips for Various Applications", *Thermochimica Acta*, 432:192-201 (2005).
Vanden Poel et al., "Performance and calibration of the flash DSC1, a new, MEMS-based fast scanning calorimeter", *Journal of Thermal Analysis and Calorimetry*, 110(3):1533-1546 (Dec. 2012).
Wang et al., "A MEMS Isothermal Titration Biocalorimeter", 16th International Conference on Miniaturized Systems for Chemistry and Life Sciences, pp. 195-197 (Oct. 28-Nov. 1, 2012) Okinawa, Japan.
Wang, et al., "A MEMS Differential Calorimeter for Biomolecular Characterization", 18th IEEE International Conference on Micro Electro Mechanical Systems, pp. 814-817 (Jan. 30-Feb. 3, 2005).
Wang, et al., "A MEMS Differential Scanning Calorimeter for Thermodynamic Characterization of Biomolecules", 24th International Conference on Micro Electro Mechanical Systems, pp. 821-824 (Jan. 2011).
Wang, et al., "A MEMS Thermal Biosensor for Metabolic Monitoring Applications", *Journal of Microelectromechanical Systems*, 17(2):318-327 (Apr. 2008).
Wang, et al., "Demonstration of MEMS-Based Differential Scanning Calorimetry for Determining Thermodynamic Properties of Biomolecules", *Sensors and Actuators B: Chemical*, 134(2):953-958 (Sep. 2008).
Wunderlich, "Quasi-Isothermal Temperature-Modulated Differential Scanning Calorimetry (TMDSC) for the Separation of Reversible and Irreversible Thermodynamic Changes in Glass Transition and Melting Ranges of Flexible Macromolecules", *Pure and Applied Chemistry*, 81(10):1931-1952 (2009).
Youssef, et al., "MEMS Scanning Calorimeter with Serpentine-shaped Platinum Resistors for Characterization of Microsamples", *Journal of Microelectromechanical Systems*, 18(2):414-423 (Apr. 2009).
U.S. Appl. No. 14/957,869, filed Dec. 3, 2015 Lin et al.
U.S. Appl. No. 13/972,783, Nov. 1, 2016 Issue Fee Payment.
U.S. Appl. No. 13/972,783, Aug. 26, 2016 Notice of Allowance.
Partial European Search Report dated Apr. 18, 2017 in Application No. EP 14807720.
Yuan et al., "A polymer-based MEMS differential scanning calorimeter," 2014 IEEE 27th International Conference on Micro Electro Mechanical Systems (MEMS), IEEE, pp. 306-309 (2014).
U.S. Appl. No. 13/972,783, Sep. 17, 2015 Non-Final Office Action.
JP Office Action dated Aug. 18, 2015 in JP Patent Application No. 2013-554690.
U.S. Appl. No. 14/957,869 dated Dec. 29, 2017 Non-Final Office Action.

* cited by examiner

| | Temperature (°C) | Stoichiometry (N) | $K_B$ (M$^{-1}$) | $\Delta H$ (kJ/mol) |
|---|---|---|---|---|
| Our results | 23 | 1.00 | ~6.0x10$^3$ | 30.0 |
| | 35 | 1.05 | ~2.8x10$^3$ | 27.8 |
| Published data* | 25 | 1.01 | 5.63x10$^3$ | 29.9 |
| | 40 | 0.97 | 3.17x10$^3$ | 29.4 |

FIG. 12

* Data source: www.microcalorimetry.com.

|  | Temperature (°C) | Stoichiometry (n) | K (M$^{-1}$) | ΔH (kJ/mol) |
|---|---|---|---|---|
| Our results | 23 | 1.01 | ~9.0x10$^4$ | 52.3 |
|  | 35 | 1.07 | ~4.0x10$^4$ | 56 |
| Published data* | 28 | 1.00 | 8.27x10$^4$ | 51.4 |
|  | 38 | 1.04 | 4.85x10$^4$ | 57.5 |

FIG. 14

MEMS-BASED ISOTHERMAL TITRATION CALORIMETRY

CROSS-REFERENCE TO RELATED APPLICATIONS

This application is a continuation of PCT/US13/051910, filed Jul. 24, 2013, which is based on and claims priority to U.S. Provisional Application Ser. No. 61/675,025 filed on Jul. 24, 2012, and U.S. Provisional Application Ser. No. 61/769,591 filed on Feb. 26, 2013, all of which are incorporated herein in their entireties.

STATEMENT REGARDING FEDERALLY SPONSORED RESEARCH

This invention was made with government support under Grant Nos. DBI-0650020 and CBET-0854030 awarded by the U.S. National Science Foundation. The United States government has certain rights in the invention.

BACKGROUND

Isothermal titration calorimetry (ITC) directly measures heat evolved in a biochemical reaction as a function of the molar reactant ratio. It can simultaneously determine all binding parameters within a single set of experiments, and thus provides an efficient, high-precision, label-free method for characterization of biomolecular reactions. ITC can be used for applications in fundamental sciences as well as drug discovery and biotherapeutics development.

Certain ITC instruments, however, have been limited by complicated structural design, slow thermal response, and large sample and reagent composition. These issues can potentially be addressed by miniaturization via Microelectromechanical Systems (MEMS) technology. MEMS-based calorimetric devices can have unique advantages over convention instruments, including reduced sample consumption, rapid time response, and improved throughput. While MEMS technology holds the potential in improved biocalorimetry for characterization of biomolecular interactions, this opportunity has not been fully explored. One issue with MEMS calorimetric devices can be the inadequate capability of handling liquid biochemical samples, representing by their general use for solid- or gas-phase samples or for liquid-phase samples without fluidic confinement or integrating with off-chip external flow cells.

By integrating microfluidic functionalities and MEMS-based thermal transduction, certain microfluidic calorimeters featuring sensitive detection of minimized volumes of liquid samples have been developed. The calorimetric sensing in such devices can be achieved through IR thermography, mechanical resonation, or integrated thin-film thermal sensors such as a resistor or a thermopile. In terms of microfluidic handling, there are generally two types of microfluidic calorimeters: flow-through calorimeters in which micro-chambers or channels are used as biological reactors while sample solutions are introduced by continuous flows, and droplet-based calorimeters in which discrete sample droplets are generated and transported to a surface for thermal detection. However, when used for characterization of biomolecular interactions, the flow-through calorimeters can consume considerable amount of samples and conduct measurements without well-defined volumes, making it difficult to obtain quantitative information associated with the reaction; while the droplet-based calorimeters can have complicated design due to on-chip droplet generation and manipulation, and can be affected by energy dissipation via evaporation.

In addition, with the function of titration, i.e., introduction of reactants at controlled molar ratios, incorporated into microfluidic calorimeters, there have been attempts of integrated ITC measurements of biochemical interactions on MEMS devices. By continuous in-channel delivery of reactants with varying molar rates to a flow-focusing junction, the heat flux upon the chemical reaction can be measured and used to calculate the enthalpy change. By varying the concentrations of the reactant solutions that were deposited to form individual droplets, the reaction heat can be measured as a function of reactants' molar ratio. Also by sequential injections of small droplets containing a reactant to a larger droplet containing the other reactant, the reaction heat per injection can be measured in real time. However, such devices can be generally difficult to accurately control the environment where the reactions are measured.

SUMMARY

The disclosed subject matter provides microelectromechanical systems-based calorimetric devices for characterization of biomolecular interactions. In an exemplary embodiment, a device includes a first micromixer, a second micromixer, a thermally-isolated reaction chamber, a thermally-isolated reference chamber, and a thermoelectric sensor. The thermally-isolated reaction chamber is in fluid contact with the first micromixer. The thermally-isolated reference chamber is in fluid contact with the second micromixer. The thermoelectric sensor is configured to measure at least one temperature value associated with reaction chamber and the reference chamber.

The first and second micromixers can be passive chaotic micromixers. For example, the first and second micromixers can be formed from a serpentine channel with herringbone shaped ridges on the ceiling thereof. The device can further include a first inlet a second inlet in fluid contact with the first micromixer, and a third inlet and a fourth inlet in fluid contact with the second micromixer.

The reaction chamber and reference chamber can be microchambers such as polydimethylsiloxane microchambers. The reaction chamber and reference chamber can be serpentine chambers. The reaction chamber and reference chamber can be disposed on a diaphragm such as a polyimide diaphragm that serves as a base for the reaction chamber and the reference chamber.

In accordance with an exemplary embodiment of the disclosed subject matter, the thermoelectric sensor can be a thermopile. The thermopile can be, for example, an antimony-bismuth thermopile. A first thermopile junction can be located on a first side of the reaction chamber, while a second thermopile junction can be located on the first side of the reference chamber.

The reaction chamber and reference chamber can be surrounded by an air cavity. In accordance with an exemplary embodiment of the disclosed subject matter, the air cavity can include a serpentine channel. The device can further include a temperature sensor and a heater for the reaction chamber and the reference chamber.

In accordance with an exemplary embodiment of the disclosed subject matter, the at least one temperature metric can be a differential temperature between the reaction chamber and the reference chamber. In other embodiments, the at least one temperature metric can be a temperature of the reaction chamber and a temperature of the reference chamber.

The disclosed subject matter further provides microelectromechanical systems-based methods for characterization of a biomolecular interaction between a first solution and a second solution. In one example, a method includes mixing the first solution and the second solution to form a reaction solution, mixing the first solution and a buffer solution to form a reference solution, and measuring a differential temperature between a reaction chamber containing the reaction solution and a reference chamber containing the reference solution. The differential temperature can be measured using a thermoelectric sensor such as a thermopile on the microelectromechanical systems-based device.

In accordance with an exemplary embodiment of the disclosed subject matter, micromixers on the microelectromechanical systems-based device (e.g., passive chaotic micromixers) can be used to mix the first and second solutions.

The method can further include computing a differential power based at least in part on the differential temperature. At least one thermodynamic reaction parameter can be calculated based at least in part on the differential power. The thermodynamic reaction parameter can be, for example, an equilibrium binding constant, a stoichiometry, or a molar enthalpy change.

A baseline temperature differential between the reaction chamber and the reference chamber can be measured prior to the introduction of the reaction solution and the reference solution. The baseline temperature differential can then be subtracted from the differential temperature for error correction. The device can also be calibrated using an on-chip heater.

The disclosed subject matter further provides microelectromechanical systems-based calorimetric devices for characterization of biomolecular reactions. In an exemplary embodiment, a device includes first mixing means for mixing a first solution and a second solution, second mixing means for mixing the first solution and a buffer solution, a thermally-isolated reaction chamber in fluid contact with the first mixing means, a thermally-isolated reference chamber in fluid contact with the second mixing means, and detection means for measuring a differential temperature between the reaction chamber and the reference chamber. The device can further include computing means for computing a differential power based at least in part on the differential temperature, and calculating means for calculating at least one thermodynamic reaction parameter based at least in part on the differential power.

The accompanying drawings, which are incorporated and constitute part of this disclosure, illustrate the various exemplary embodiments of the present disclosed subject matter and serve to explain its principles.

BRIEF DESCRIPTION OF THE DRAWINGS

FIG. 12 shows a comparison between reaction parameters obtained in accordance with an embodiment of the disclosed subject matter and published data reflecting reaction parameters obtained using commercial calorimeters.

FIG. 14 shows a second comparison between reaction parameters obtained in accordance with an embodiment of the disclosed subject matter and published data reflecting reaction parameters obtained using commercial calorimeters.

DETAILED DESCRIPTION

The disclosed subject matter provides microelectromechanical systems-based calorimeters, and methods for using such devices.

Figure 1A:
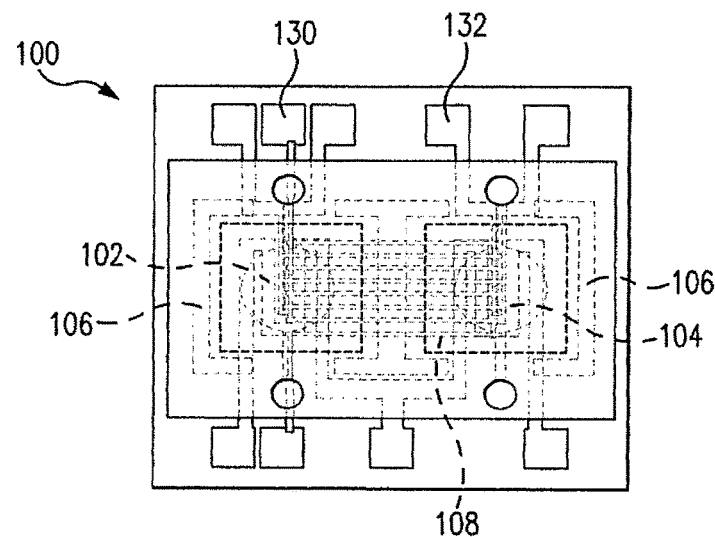
FIG. 1A illustrates an exemplary embodiment of the calorimeter in accordance with the disclosed subject matter.
Figure 1B:
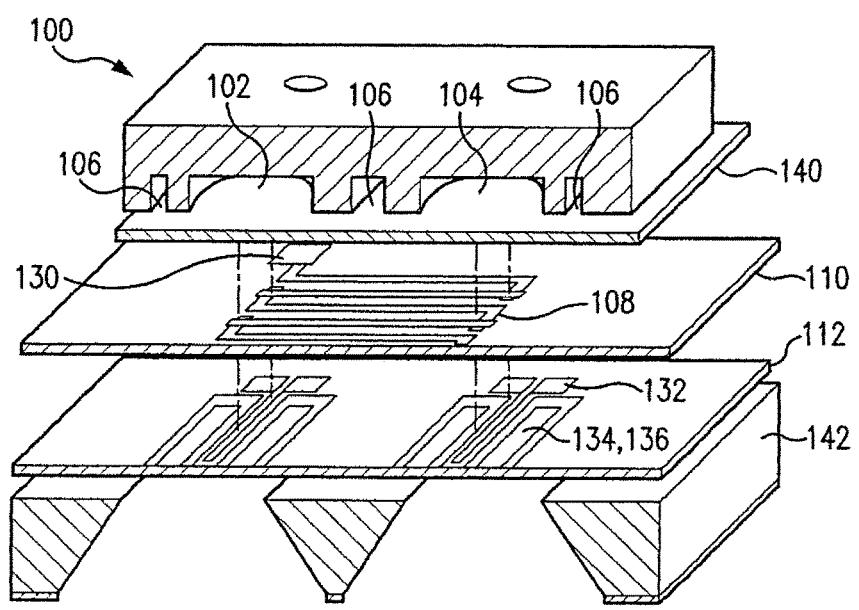
FIG. 1B illustrates a cross-section view of the calorimeter in FIG. 1A.
Figure 1C:
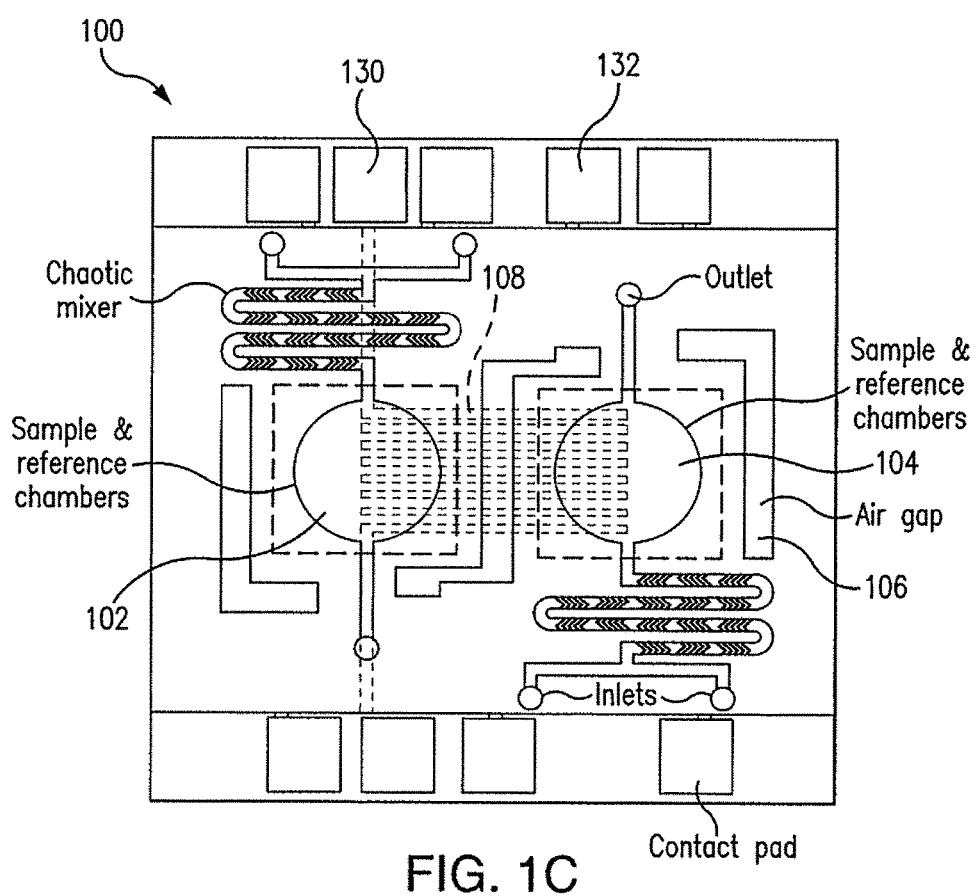
FIG. 1C illustrates a different view of the calorimeter in FIG. 1A.

A first exemplary embodiment of a device in accordance with the disclosed subject matter is illustrated in FIGS. 1A-1C. As shown in FIG. 1A, the device 100 includes two chambers: a reference chamber 102 and a reaction chamber 104. The reference chamber 102 and reaction chamber 104 in FIG. 1A are shown as having a circular shape. However, a wide variety of geometric configurations can be used in accordance with the disclose subject matter. Reference chamber 102 and reaction chamber 104 can be microchambers. Various materials suitable for microfabrication and thermal isolation can be used to construct the chambers. For example, a material having sufficient thermal stability within the temperature range of interest (e.g., −10° C. to 90° C.), reasonably strong bonding with the substrate surface, and minimized adsorption of macromolecules (e.g., proteins) can be used. The microchambers can be formed from polymers such as SU-8, parylene, polycarbonate, and polyether ether ketone (PEEK). In accordance with an exemplary embodiment of the disclosed subject matter, the microchambers can be formed from polydimethylsiloxane.

Each of the microchambers can be thermally isolated. For example, microchambers 102 and 104 are surrounded by air cavities 106 for effective thermal isolation. Air cavities 106 are also formed from polydimethylsiloxane. In accordance with embodiments of the disclosed subject matter, the microchambers can be thermally isolated by residing on a freestanding structure constructed from materials such as a polymeric material having low thermal conductivity. In order to further isolate the microchambers from the ambient environment, the device 100 can be enclosed by a thermal enclosure (e.g., the device 100 can be placed in a vacuum to minimize thermal energy dissipation to the ambient environment).

The device can also include a thermoelectric sensor. In accordance with the embodiment illustrated in FIG. 1A, the thermoelectric sensor is a thermopile 108. The thermopile 108 includes hot and cold junctions. The hot and cold junctions of the thermopile 108 are located underneath the microchambers 102, 104 in order to measure the thermal power difference between the reference chamber 102 and the reaction chamber 104. For example, the thermopile 108 can include a plurality of elongated segments of dissimilar materials, where adjacent segments of dissimilar materials are joined together at opposite ends, thereby forming thermocouple junctions. The thermocouple junctions underneath each chamber can be aligned to the central axis of each chamber. The thermoelectric sensor can have a thermoelectric sensitivity of greater than 80 µV/° C. per thermocouple.

For example, as shown in FIG. 1B, the thermopile 108 can be embedded into a layer located underneath the microchambers 102, 104. In particular, the microchambers 102, 104 can be situated on a diaphragm including a top layer 110 and a bottom layer 112. The layers of the diaphragm are integrated, but for purposes of illustration are shown in FIG. 1B as separate layers. The top layer 110 and bottom layer 112 can be made from a thermally stable and electrically insulating material having good thermal isolation properties, as well as thermal and mechanical stability to withstand the thermal cycles required by repeated calorimetric measurements. In particular embodiments, the diaphragm can be made of a material having a glass transition temperature greater than 150° C. and a thermal decomposition temperature greater than 250° C. For example, polymers including polyimide, parylene, polyester, SU-8, PDMS, and polytetrafluoroethylene can be used to fabricate the diaphragm. In accordance with one embodiment of the disclosed subject matter, top layer 110 and bottom layer 112 can be polydimethylsiloxane layers. In other embodiments, polyimide is selected as the diaphragm material because of its excellent mechanical stiffness (Young's modulus: 2.5 GPa) and thermal stability (glass transition temperature: 285° C.).

In accordance with some embodiments of the disclosed subject matter, an interfacing layer 140 between the microchambers and the diaphragm can be made from a mixture of the materials for the microchambers 102, 104 and the materials for the top and bottom layers 110, 112, e.g., a mixture of polyimide and PDMS.

The diaphragm can be situated on another solid substrate 142, e.g., a silicon wafer. To improve thermal isolation, the solid substrate in the area underneath the bottom side of the diaphragm corresponding to a cross section of each of the microchambers 102, 104 can be removed, such that the portion of the diaphragm under each of the microchambers 102, 104 does not contact the solid substrate 142 (i.e., it only contacts air, which is believed the best thermal insulator).

The thermopile 108 can be located between the top layer 110 and the bottom layer 112. Various materials can be used to form the thermopile 108. For example, in accordance with one embodiment of the disclosed subject matter the thermopile 108 is a thin-film antimony-bismuth thermopile. The material for the thermopile 108 can also be chosen to have high electrical conductivity, low thermal conductivity, and high Seebeck coefficient. For example, the material for the thermopile 108 can also include pairs of materials providing high thermoelectric efficiency, such as n-type and p-type bismuth telluride, and n-type and p-type antimony telluride. Many metals, semiconductors, and their compounds, including chrome, nickel, bismuth, antimony, bismuth telluride, and antimony telluride, can be used for fabricating the thermopile 108.

In accordance with another embodiment of the disclosed subject matter, the thermoelectric sensor can include a reaction chamber thermoelectric sensor and a reference chamber thermoelectric sensor, each of which measures the absolute temperature of the reaction in the respective microchambers. The differential temperature can then be determined by calculating the difference between the temperatures measured by the thermoelectric sensors.

Figure 2:
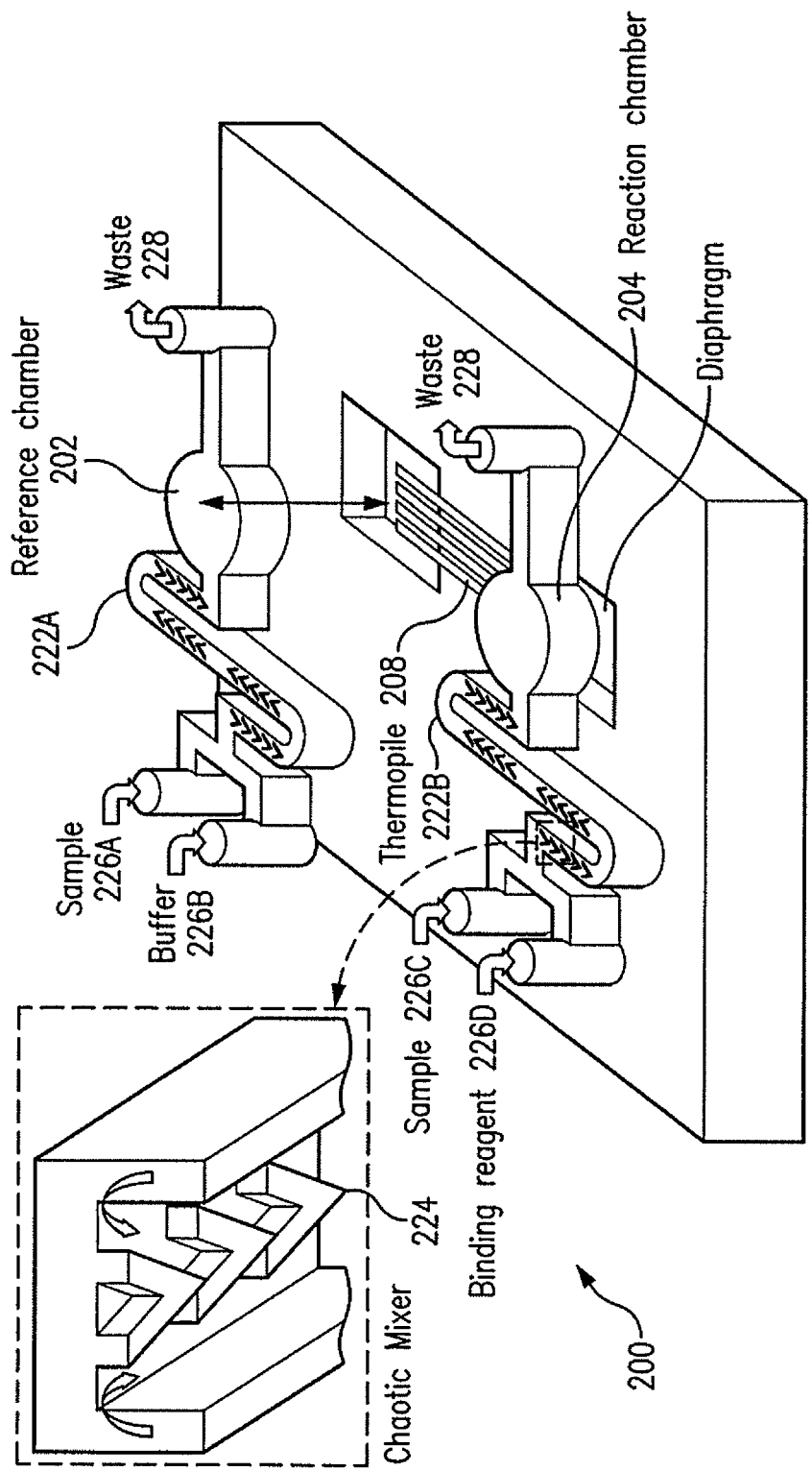
FIG. 2 illustrates a simplified view of the flow pathways of the calorimeter of FIG. 1A.

The devices in accordance with the disclosed subject matter can further include one or more mixers. The mixers can be, for example, passive chaotic micromixers. With reference to FIG. 2, a simplified view of a device 200 in accordance with the disclosed subject matter is shown. The device 200 includes micromixers 222A, 222B in the form of a serpentine channel. However, other configurations can be used for the micromixers. The micromixers 222A, 222B include protrusions 224 in the ceiling of the serpentine channel for generating a chaotic flow pattern that induces mixing of the incoming streams. The protrusions can be, for example, herringbone-shaped ridges, as shown in FIG. 2.

The device 200 can also include inlets 226A-226D for introducing samples, reagents, buffers, and the like into the micromixers 222A, 222B. The inputs 226A-226D can be implemented in numerous configurations. The inlets 226A-226D can be connected to channels that carry the samples, reagents, buffers, and the like from the inputs to the micromixers 222A, 222B. The samples, reagents, buffers, and the like can be introduced as described below in connection with exemplary embodiments of the disclosed methods.

The device 200 can also include waste disposal outlets 228 for removing the samples, reagents, buffers, and the like from the microchambers 202, 204.

Figure 3:
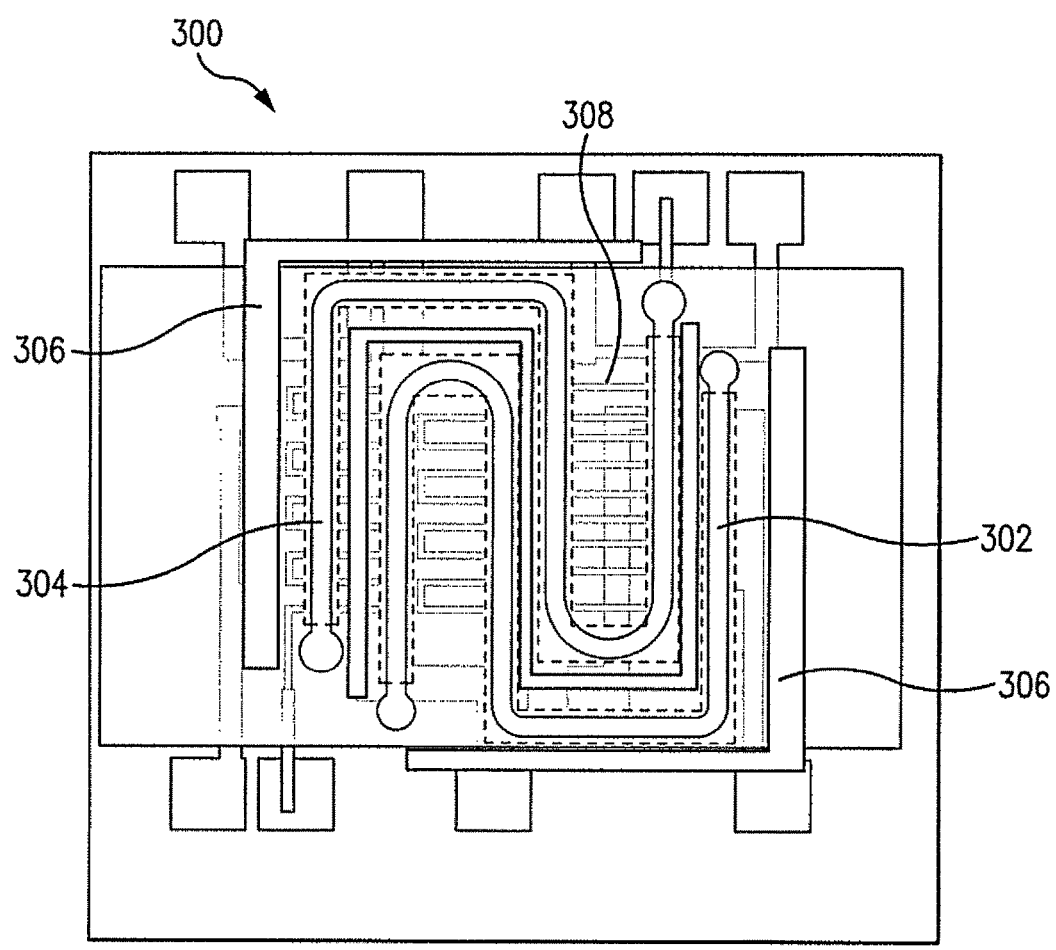
FIG. 3 illustrates a second exemplary embodiment of the calorimeter in accordance with the disclosed subject matter.

With reference to FIG. 3, a second embodiment of a device in accordance with the disclosed subject matter is shown. The device 300 includes a serpentine reference chamber 302 and a serpentine reaction chamber 304. The reference chamber 302 and reaction chamber 304 are thermally isolated by the air cavities 306. The thermopile 308 is also shown. The use of serpentine microchambers 302, 304 allows for a greater number of thermopile junctions and can improve thermal isolation.

With further reference to FIG. 1A, the device can also include one or more contact pads 130, 132. The contact pads can provide an interface between the device and various electronic circuits. For example, contact pad 130 is coupled to the thermopile 108. In particular, the ends of thermopile 108 can be designed to cover part of the contact pad 130. The adhesion between the ends of thermopile 108 and contact pad 130 can be enhanced by surface roughening or chemical modification. A designed external packaging via a flip chip bonding method can also be implemented. The output of the thermopile 108 is a voltage indicative of a differential temperature between the reference chamber 102 and the reaction chamber 104. The contact pad 130 can also be coupled to an electronic circuit for measuring and analyzing the output voltage. The term "coupled," as used herein, includes direct coupling such as direct electrical contact (e.g., through a soldered wire or alligator clip) as well as indirect coupling, as through wireless communication.

Figure 5:
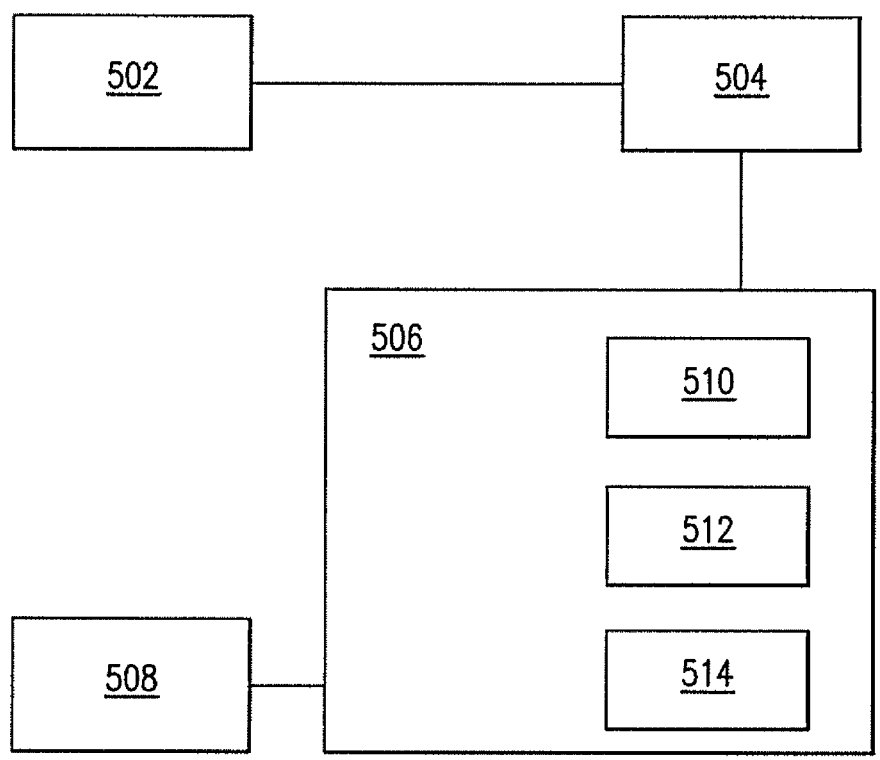
FIG. 5 illustrates a system for calculating thermodynamic properties of a reaction based on the measured differential temperature in accordance with one embodiment of the disclosed subject matter.
Figure 6A:
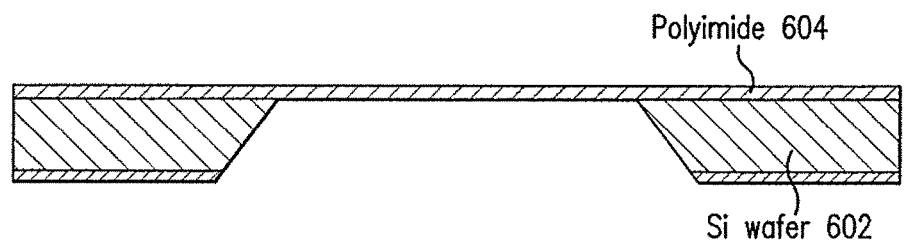
FIG. 6A-6E illustrates a method for fabricating a calorimeter in accordance with one embodiment of the disclosed subject matter.
Figure 6B:
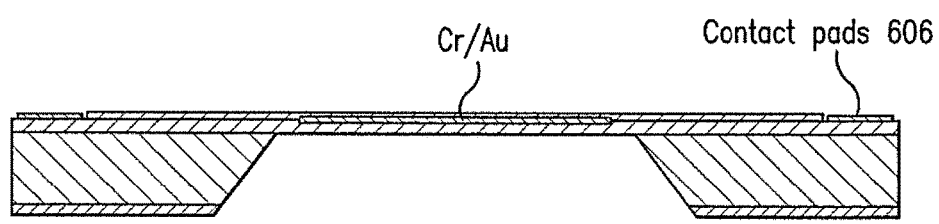
Figure 6C:
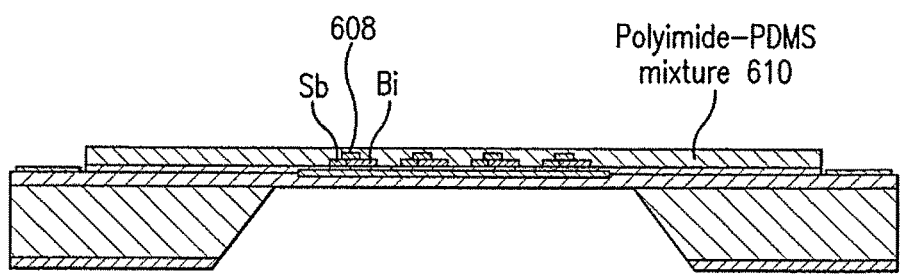
Figure 6D:
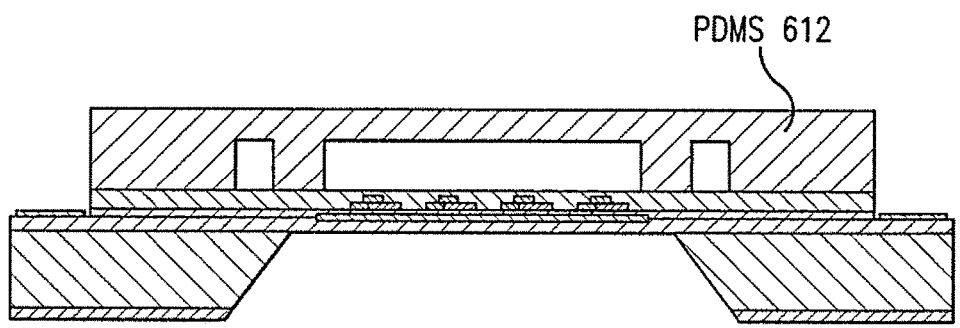
Figure 6E:
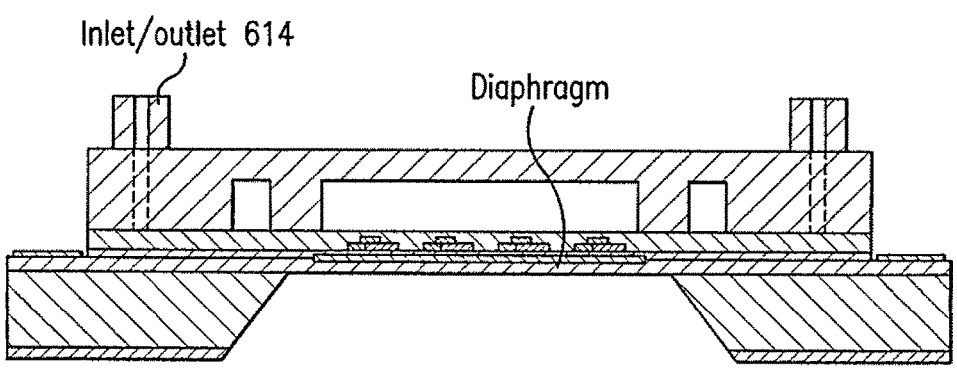

An electronic circuit that can be coupled to contact pad 130 in accordance with one embodiment of the disclosed subject matter is illustrated in FIG. 5. Contact pad 502 acts as the interface between the calorimeter and the one or more electronic circuits 500. The contact pad 502 is coupled to a voltmeter 504. The term "voltmeter," as used herein, is intended to encompass any instrument that can be used to measure voltage, either directly or indirectly, including voltmeters and multimeters. The voltmeter 504 can include at least one processor.

The voltmeter 504 can be coupled to a calculation device 506. The calculation device includes one or more processors formed by one or more electronic circuits. The calculation device 506 can be coupled to a storage device 508.

The calculation device 506, as well as each of the components thereof, can be implemented in a variety of ways as known in the art. For example, each of the components of the calculation device can be implemented using an integrated single processor. Alternatively, each component can be implemented on a separate processor. One or more components of the calculation device 506 can also be combined with the voltmeter 504 rather than being a separate device.

The at least one processor can include one or more electronic circuits. The one or more electronic circuits can be designed so as to implement the disclosed subject matter using hardware only. Alternatively, the processor can be designed to carry out instructions specified by computer code stored in a the storage device 508. The storage device 508 can be a hard drive, a removable storage medium, or any other non-transitory storage media. Such non-transitory computer readable media can store instructions that, upon execution, cause the at least one processor to perform the methods as disclosed herein.

The calculation device 506 can include a number of components, including an adjustment component 510 for adjusting the output voltage based on a baseline in output voltage, a thermal power differential component 512 for determining a thermal power differential based on the output voltage, and a reaction characterization component 514 for calculating thermodynamic reaction parameters based on the thermal power differential.

With further reference to FIG. 1A, contact pads 132 can be connected to a sensor 134 and a heater 136. The sensor 134 and the heater 136 can be used for in-situ temperature monitoring and on-chip device calibration. The sensor 134 and heater 136 can be a single integrated unit. For example, the device can include an integrated thin-film resistive micro-temperature sensor and heater. The sensor 134 can monitor the chamber temperatures in real time while the heater 136 can provide heating to the chamber to generate a constant differential power for calorimetric calibration. The sensor 134 and heater 136 can be, for example, a thin-film resistor that can be fabricated using MEMS technology. In practice, Joule heating can be generated by passing an electrical current through the heater 136. The local temperature can then be determined by the sensor 134 based on a calibrated relationship between the temperature and the electrical resistance.

The heater 136 can also be used for temperature modulation. For example, in accordance with an embodiment of the disclosed subject matter, a temporally periodic variation, or AC modulated heating, can be introduced to the reference and sample materials during heating of the thermal enclosure. This can lead to temperature modulation, which allows thermal relaxation of biomolecules, as well as allowing the biochemical reaction signal to be readily extracted at the modulation frequency in the broad-band background noise. The heater 136 can be controlled by a wave generator which can provide different frequency, magnitude and other parameters for on-chip heating.

The material of the microheaters can be chosen from a variety of metals or metal alloys, for example, chromium/gold (Cr/Au). The contact pads 132 can be connected to an electronic circuit similar to the circuit described in connection with FIG. 5 in order to performing temperature monitoring and on-chip device calibration functions as disclosed herein.

With reference to FIG. 6A-6E, an exemplary method of fabricating a device in accordance with the disclosed subject matter is shown. The process begins with a substrate 602 such as a silicon wafer. A polyimide layer 604 is layered on the substrate 602 in 6(a). The polyimide layer can be coated on the substrate by spin-coating. A pair of cavities can also be etched by TMAH into the backside of the solid substrate in the areas that correspond to the calorimetric chambers. After curing the polyimide layer, microheaters and temperature sensors can be deposited by thermal evaporation of a metal or metal alloy, e.g., Cr/Au. Contact pads 606 can then be layered on top of the polyimide layer 604 in 6(b). The contact pads can be formed from a variety of materials, including chromium, gold, and mixtures thereof. The thermopile 608 can then be added to the device by thermal evaporation and patterned using a standard lift-off process. The thermopile 608 can be an antimony-bismuth thermopile. A top layer 610 can then be formed on top of the thermopile 608 in 6(c), for example, by spin-coating. The top layer 610 can be formed from a polyimide-PDMS mixture. A layer of PDMS 612 can then be placed on top of the top layer 610 in 6(d). The layer of PDMS 612 can include microchambers and micromixers. In particular, micromolding techniques can be used to form microchambers and micromixers on top of the top layer 610. Finally, inlets and outlets 614 can be disposed on the device in 6(e).

Figure 7:
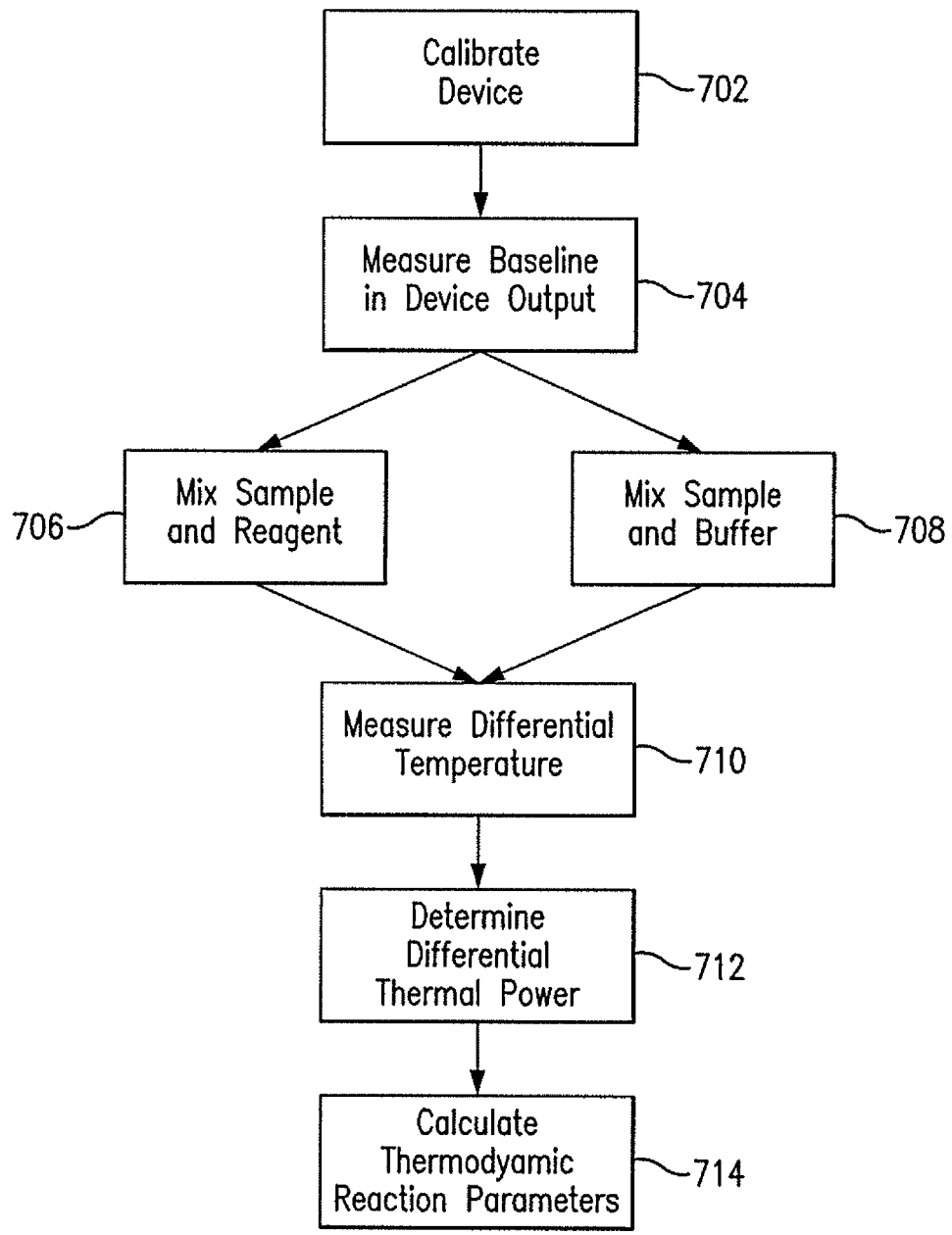
FIG. 7 is a flow chart illustrating an exemplary embodiment of a method for calculating thermodynamic reaction parameters in accordance with the disclosed subject matter.

An exemplary method for measuring a differential temperature and characterizing a reaction in accordance with an embodiment of the disclosed subject matter is shown in FIG. 7. Broadly, the method can include calibrating the device, measuring a baseline in device output, mixing the sample and the reactant, mixing the sample and the buffer, measuring a differential temperature, determining the thermal power, and calculating the thermodynamic reaction parameters.

To begin, the calorimetric device is calibrated at 702. For examples, calibration techniques known in the art are described in A MEMS Differential-Scanning-Calorimetric Sensor for Thermodynamic Characterization of Biomolecules by Bin Wang and Qiao Lin, J. Microelectromechanical Systems 21:5, 1165-1171 (October 2012), which is incorporated by reference herein in its entirety for all purposes.

The baseline in device output can then be measured at 704. For example, if a thermopile is used to measure the differential temperature, the thermopile output voltage in the absence of a reaction can be measured. This can be accomplished by introducing a mixture of sample and buffer solutions into each of the chambers. The baseline in device output can then be stored in storage device 508 as shown in FIG. 5 for future use.

The sample and the reactant can then be mixed at 706. The sample and the buffer can be mixed substantially simultaneously at 708. Mixing can be accomplished using a passive chaotic mixer such as the one illustrated in FIG. 2. Using the device 200, the sample is introduced into inlets 226A and 226C, the buffer is introduced into inlet 226B, and the reactant is introduced into inlet 226D. The sample and the reactant are passively mixed in mixer 222B and deposited into the reaction chamber 204. The sample and the buffer are passively mixed in mixer 222A and deposited into the reference chamber 202. Any titration techniques known in the art for use with Isothermal Titration Calorimetry (ITC) can be used.

In accordance with an embodiment of the disclosed subject matter, titration on the MEMS device can be performed with a series of discrete reactions, with each reaction having a specific molar ratio of the reactants. Liquid cartridge segments can be used for introduction of reactants. For example, binding reagents in different concentrations can be prepared while the sample is prepared in a fixed concentration. As such, the molar ratio can be varied with the volume of sample and binding reagent maintained identical (e.g., 0.5 μL). The sample and binding reagent can each be loaded in a long access tubing sequentially separated by air (such that the molar ratio changes along with the sequence of reactant segments). The access tubes can be driven by a multi-port syringe pump. At each molar ratio, the syringe pump can deliver the exact amount of sample and reagent into the reaction chamber for heat measurement, as well as sample and buffer into the reference chamber. Buffer segments can also be added between two reactant segments in the sequence for purposes of cleaning the chamber or mixer.

With further reference to FIG. 7, the differential temperature of the reactions is measured at 710. The measurement can be accomplished using a thermoelectric sensor such as a thermopile. The thermopile can output a voltage indicative of the differential temperature. The output voltage can then be adjusted based on the baseline in device output measured at 704.

The differential temperature can then be used to determine a thermal power related to the reaction at 712. The thermal power difference $\Delta P$ can be calculated as:

$$\Delta P = \frac{\Delta U}{S} \quad (1)$$

where $\Delta U$ is the output from the thermoelectric sensor and S is the thermoelectric sensitivity, i.e., the output electrical voltage generated by unit differential thermal power.

The differential thermal power can then be used to calculate the thermodynamic reaction parameters at 714. In general, a biochemical reaction between a sample molecule M and a binding reagent X can be represented as:

$$n_1 X + n_2 M \rightarrow MX + \Delta H \quad (2)$$

where the reaction results in the product MX accompanied by a change of enthalpy $\Delta H$. In ITC, the binding reagent X is titrated, i.e., successively added in known aliquots, into the sample, while the reaction heat is measured. The reaction heat is measured. The reaction heat is used to calculate the thermodynamic properties of the reaction, including the equilibrium binding constant $K_B = [MX]/[X][M]$ (where $[\cdot]$ denotes the equilibrium concentration of the species), stoichiometry $N = n_1/n_2$, and molar enthalpy change $\Delta H$. In particular, the reaction heat can be calculated based on the differential thermal power. The biochemical reaction heat can be expressed as:

$$Q = \frac{NM_t \Delta H V_0}{2} \left[ 1 + \frac{r}{N} + \frac{1}{NK_B M_t} - \sqrt{\left(1 + \frac{r}{N} + \frac{1}{NK_B M_t}\right)^2 - \frac{4r}{N}} \right] \quad (3)$$

where Q is the biochemical reaction heat evolved at a molar ratio $r = X_t/M_t$, $V_0$ is the active volume for the reaction, $M_t$ is the total concentration of the sample, free plus bound, in the reaction cell of volume $V_0$, and $X_t$ is the total concentration of the reagent that is titrated into the sample solution.

In order to calculate the thermodynamic reaction parameters, an integral of the differential thermal power is computed. The resulting value is used as the biochemical reaction heat. A number of data points can be gathered based on the voltage measurements from a number of trials using different molar ratios. The resulting data can then be fitted to Equation (3) in order to calculate the thermodynamic reaction parameters. Fitting can be accomplished using any fitting methods as known in the art for its intended purpose.

Examples

Figure 8A:
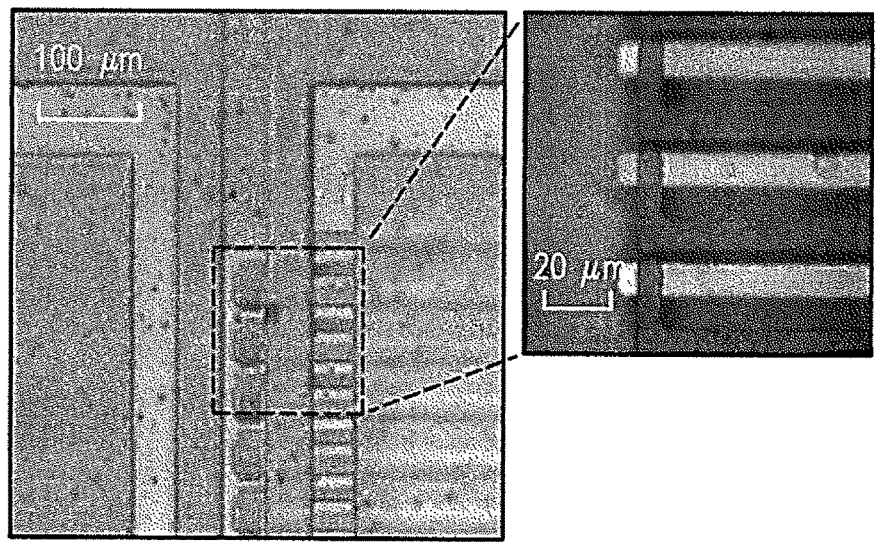
FIG. 8A-8B illustrates certain elements of a calorimeter in accordance with an exemplary embodiment of the disclosed subject matter.
Figure 8B:
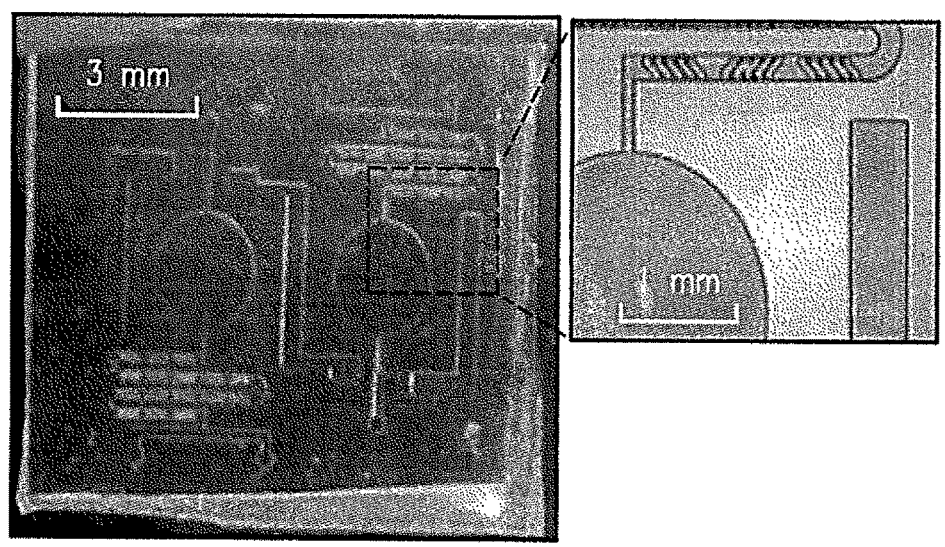

Chaotic mixers and calorimetric chambers were fabricated in a single sheet using PDMS replica technique based on multiple-layered SU-8 molding. The microfabricated device integrated a 50-junction Sb—Bi thermopile and two 0.75 μL calorimetric chambers with a center-to-center separation of 4 mm. The calorimetric chambers had a cylindrical shape with a height of 150 μm and a diameter of 2.5 mm. The chaotic mixers were serpentine microchannels (width: 200 μm, height: 150 μm, length: approximately 15 mm) with herringbone-shaped ridges on the ceiling with each having a width of 40 μm, a height of 50 μm, an orientation angle of 60° to the channel sidewall, and an edge-to-edge distance between adjacent ridges of 30 μm. The nominal resistances of the integrated resistive microheaters and temperature sensors were 40Ω and 55Ω, respectively. Certain elements of the thermal substrate and PDMS structure, including the embedded thermopile 802 and the calorimetric chamber 804 with chaotic mixer 806, are shown in FIG. 8.

To test the MEMS-IT device, a thermal enclosure was custom-built to house the device to shield the thermal disturbance from ambient, as well as provide uniform temperature control to the solutions loaded in the device. The thermal enclosure was improved with additional thermal isolation by suspending the sample stage from the base, vibration isolation by enhanced base mass and rubber buffering layer, and multiple-ports microfluidic feedthrough to the device. The temperature control of the thermal enclosure was implemented by a commercial temperature controller (Lakeshore Model 331). The device was first packaged with electrical interconnection wires and fluidic interconnection tubes before it was situated on the sample stage inside the thermal enclosure.

The on-chip microheaters, used for device calibration, were driven by a DC power supply (Agilent E3631A) and generated a constant differential heating power in the calorimetric chambers. The on-chip temperature sensors, used for in-situ temperature monitoring of the calorimetric chambers, were interrogated by a digital multimeter (Agilent 3410A). The thermopile output voltage, which is proportional to the differential temperature between the chambers, was measured by a nanovoltmeter (Agilent 34420A). The temperature monitoring of the calorimetric chambers and thermoelectric measurements were automated using a personal computer via a LabVIEW-based program. The biological sample and buffer solutions were degassed with a vacuum chamber built in-house, metered introduced into the MEMS-ITC device using a multiple-injections syringe pump (KD Scientific, KDS 220).

The device was first calibrated by measuring its steady-state and transient response to differential power generated by on-chip microheaters. Before ITC measurements, the baseline in device output, i.e., the thermopile output voltage in the absence of reaction, was measured with introduction of sample and buffer solutions to both calorimetric chambers. During ITC measurements, the thermal enclosure provided a controlled reaction temperature while the thermopile output, indicative of the differential bio-thermal power, was detected in real time, as well as the integrated micro-temperature sensor to monitor the temperatures of the calorimetric chambers. The volume of ligand and sample was fixed at 0.5 μL for each injection, while the molar ratio was adjusted by changing the concentration of ligand to be injected. The baseline in device output was always subtracted from the measurement signal for determination of thermodynamic properties of biomolecules.

The thermal time constant of the MEMS-ITC device was calibrated by applying a step differential power of 90 μW initially and then turned it off once the device output reached its equilibrium. The device output voltage was found to fit the first-order exponential growth and decay functions upon the application and removal of the differential power, respectively, from which the thermal time constant was determined to be approximately 1.5 s. In addition, the steady-state response of the device was calibrated to varying differential power, and a linear relationship showing a constant thermoelectric sensitivity of S=4.9 mV/mW was observed. The device's sensitivity was also calibrated at controller temperatures (provided by the thermal enclosure) from 20° C. to 45° C., and it was found that it remained almost unchanged with a relative standard deviation of less than 3%.

Figure 9:
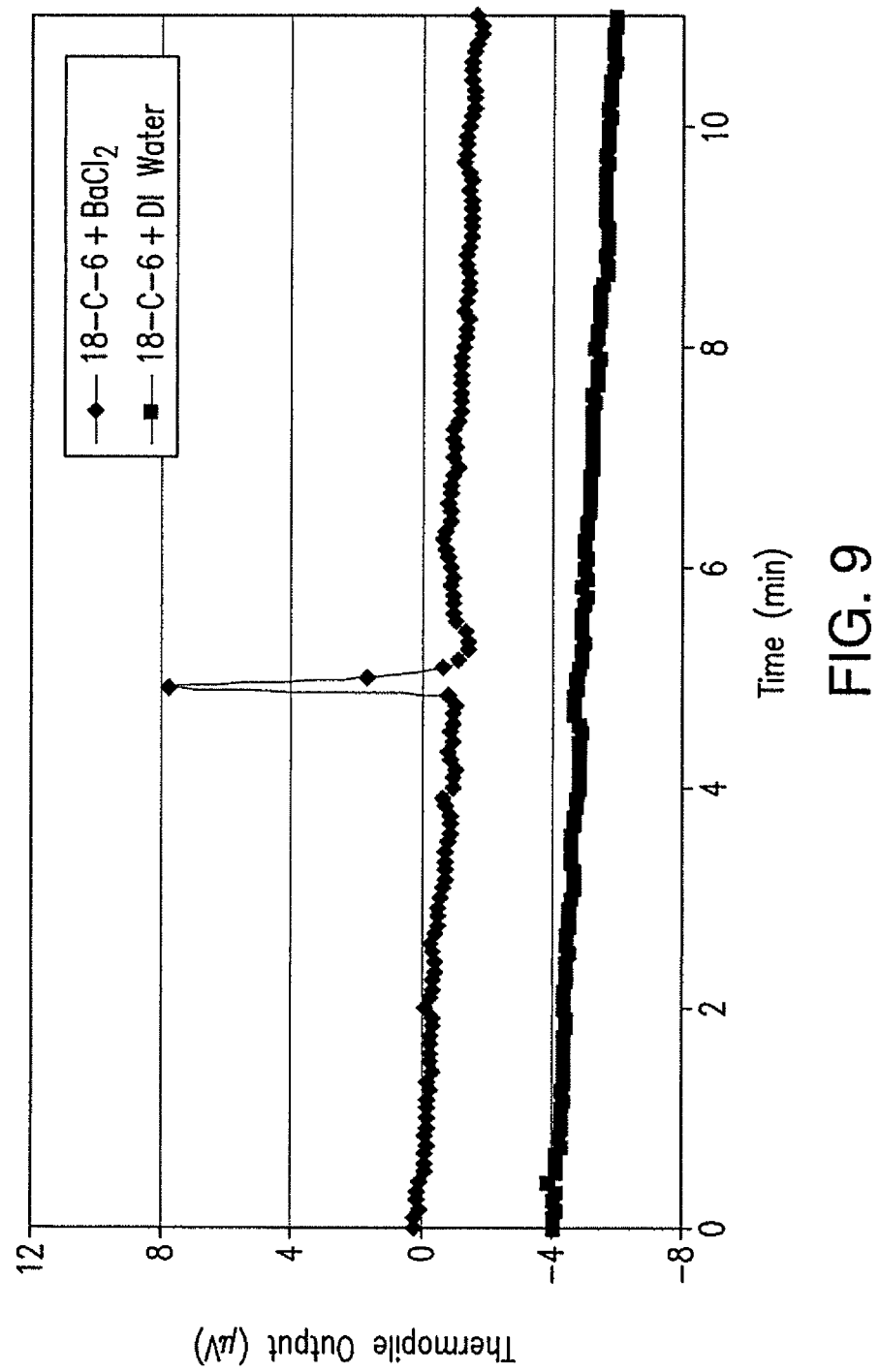
FIG. 9 illustrates a comparison of measurements of the time-resolved thermopile voltage upon introduction of 4 mM $BaCl_2$ and 5 mM 18-C-6 (each 0.5 µL) in the reaction chamber, and the signal upon introduction of sterile water and 5 mM 18-C-6 (also each 0.5 µL) in accordance with an embodiment of the disclosed subject matter.

The baseline stability and detection specificity was then tested using a standard chemical reaction of 18-Crown-6 (18-C-6) and barium chloride ($BaCl_2$) both prepared in sterile water (all chemicals from Sigma Aldrich). Using a flow rate of 50 μL/min, the solutions were injected into the calorimetric chambers within 1 s. Using a data acquisition rate of 2 $s^{-1}$ to monitor the device output in real time, no appreciable delay was observed after injection, indicating full mixing of the reactants. A comparison of the time-resolved thermopile voltage upon introduction of 4 mM $BaCl_2$ and 5 mM 18-C-6 (each 0.5 μL) in the reaction chamber, and the signal upon introduction of sterile water and 5 mM 18-C-6 (also each 0.5 μL) is shown in FIG. 9. For both measurements, the reference chamber was injected with sterile water and 5 mM 18-C-6, and a data acquisition rate of 0.2 $s^{-1}$ was used due to instrument configuration for lower background noise. The device exhibited a stable baseline throughout the measurements and a reaction-specific spike attributable to the exothermic nature of the binding between 18-C-6 and $BaCl_2$. The reaction completed in approximately 20-30 s, during which any interference from solution injection and mixing were generally negligible.

Figure 10:
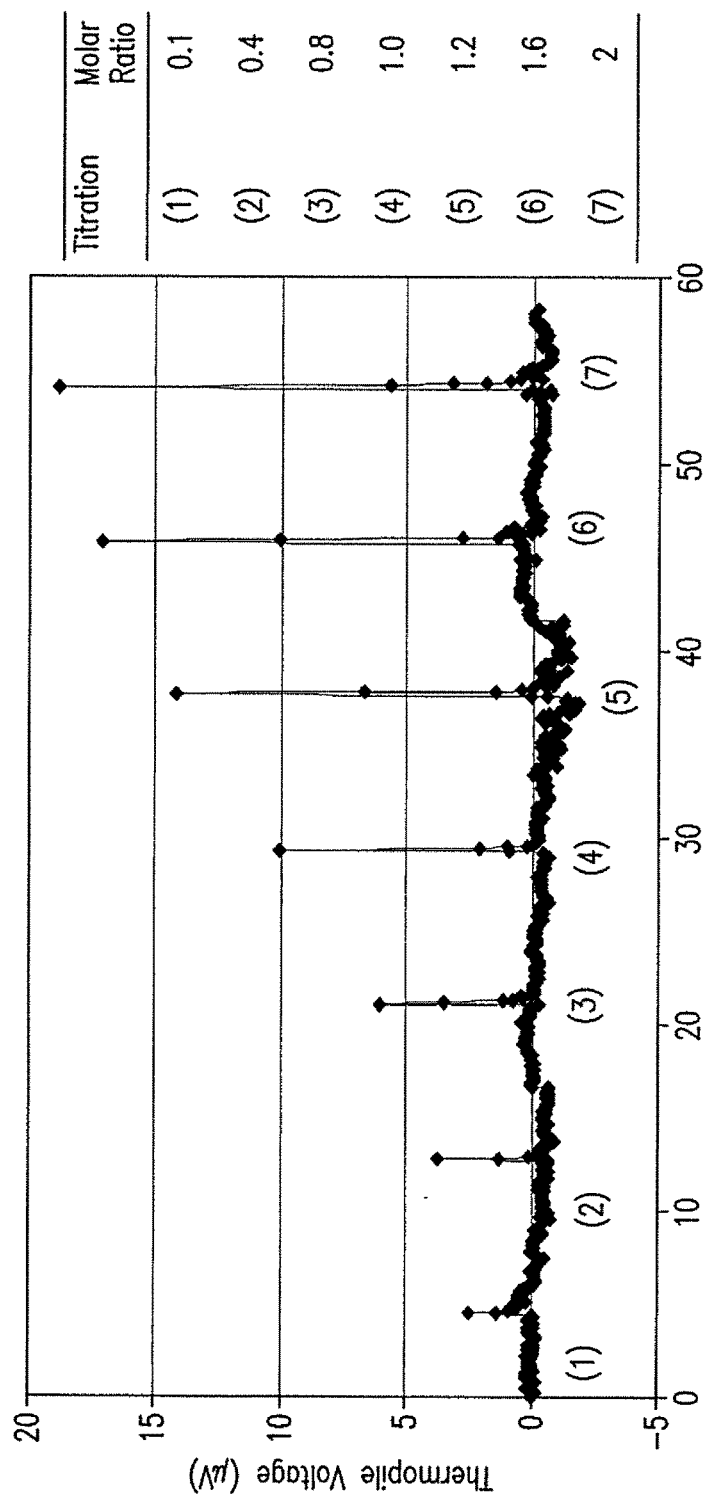
FIG. 10 illustrates the baseline-subtracted device output of a device for characterizing biochemical reactions in accordance with one embodiment of the disclosed subject matter.

The MEMS-ITC device was then used to characterize biomolecular interactions. The $BaCl_2$-18-C-6 reaction was used to validate the ITC measurements. By varying the molar mass ratio ($MBACl_2/M18$-C-6) from 0.1 to 2, the baseline-subtracted device output demonstrated spikes consistent with the titration reactions. The baseline-subtracted device output is shown in FIG. 10. Rather than measuring the heat evolved with the addition of several aliquots of $BaCl_2$ to a single sample of 18-C-6 as performed in commercial ITC instruments, the ITC experiment was performed at discrete measurements each with a definite concentration of $BaCl_2$ (0.5-10 mM) and a fixed concentration of 18-C-6 (5 mM). Each measurement was completed in approximately 5 min.

The thermopile voltage was used to calculate the bio-thermal power based on Equation 1. The bio-thermal power was then used to calculate the reaction heat by integral of the biothermal power during the process.

Figure 11:
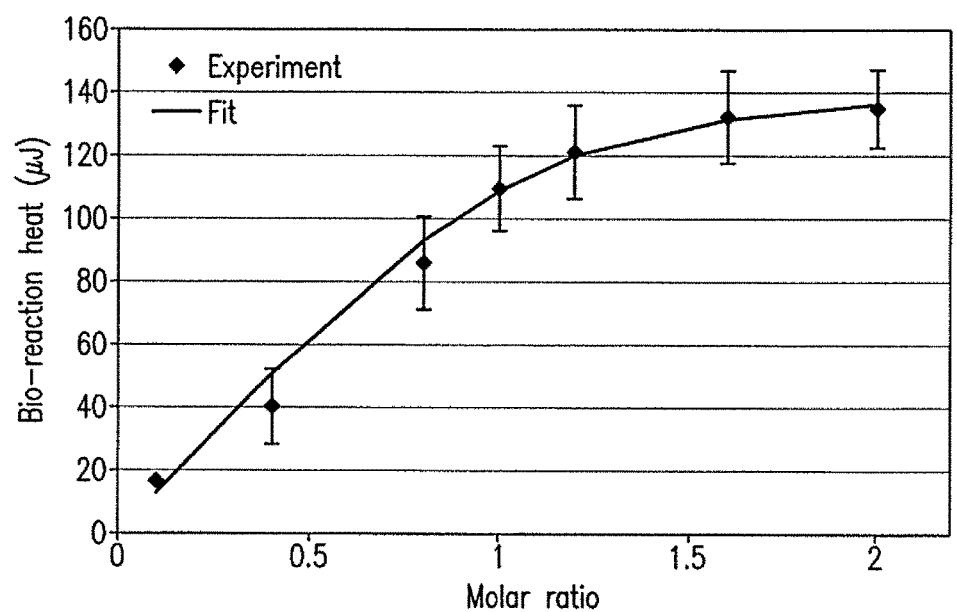
FIG. 11 illustrates the calculated reaction heat derived from the output voltage measurements in accordance with one embodiment of the disclosed subject matter.

The binding isotherm of the reaction of 18-C-6 and $BaCl_2$, as well as the fitted curve, is shown in FIG. 11, with error bars representing the standard deviation from three measurements a each molar ratio. Note that for this specific BaCl2-18-C-6 system, the device affords detectable sample concentrations approaching those of convention instruments (ca. 1 mM) with roughly three orders of magnitude reduction in volume.

ITC measurements were performed of the biological reaction of 18-C-6 and BaCl2 at controlled temperatures of 23° C. and 35° C., and the resulting binding isotherms were used to compute the temperature-dependent thermodynamic properties of N, $K_B$, and ΔH. In particular, as temperature increases from 23° C. to 35° C., N slightly increases from 1.00 to 1.05, while $K_B$ decreases from approximately 6.0× $10^{-3}$ to 2.0×$10^{-3}$ $M^{-1}$ and ΔH decreases from 30.0 o 27.8 kJ/mol, showing a trend of slightly weaker binding with temperature. These properties and their temperature dependence obtained by suitable measurements agree reasonably with published data using commercial calorimeters as shown in FIG. 12.

Figure 13:
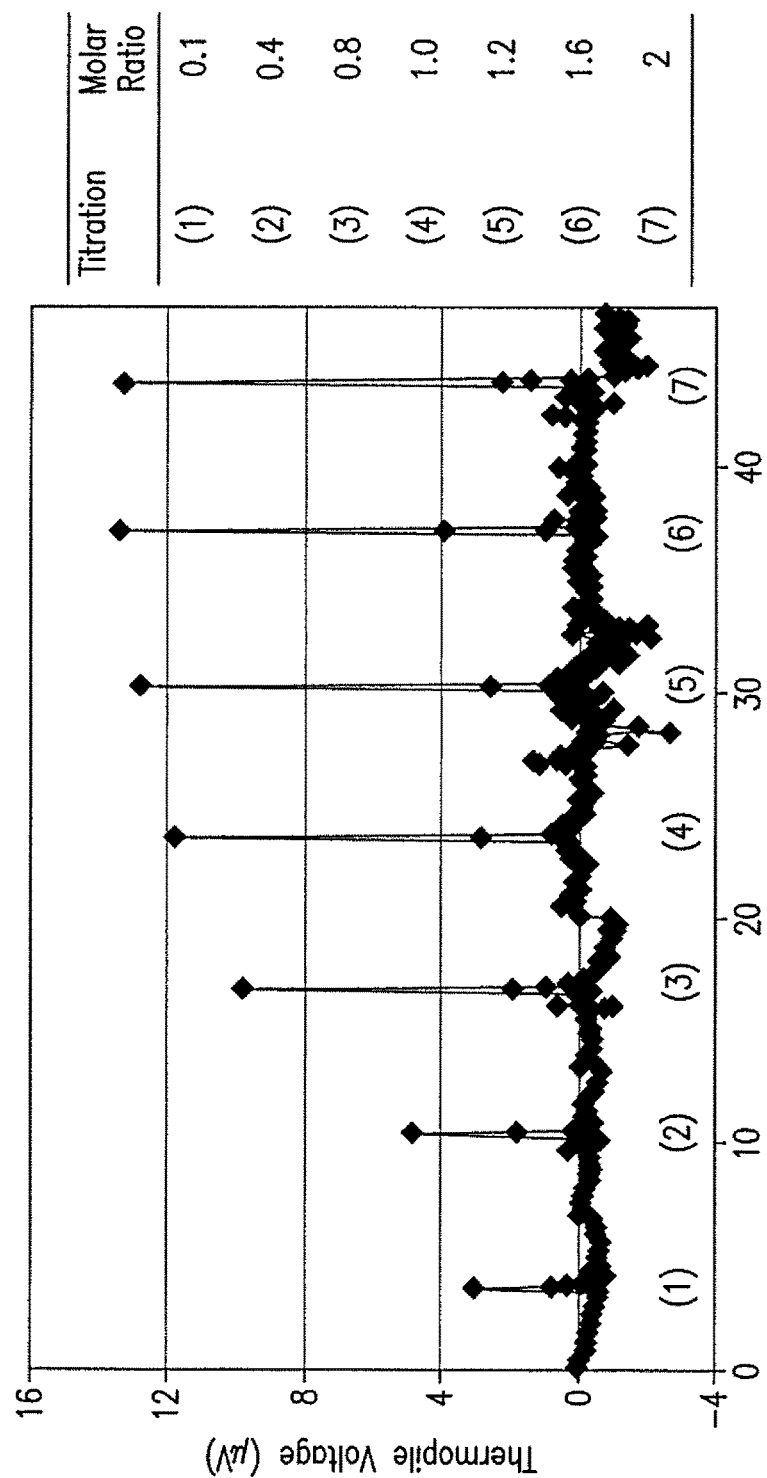
FIG. 13 illustrates device output exhibited titration-dependent spikes in correspondence to the molar ratio at varying molar ratios in accordance with an embodiment of the disclosed subject matter.

The MEMS-ITC device was further applied for characterization of biomolecular interactions, e.g., ligand-protein binding, using a demonstrative system of cytidine 2'-monophosphate (2'CMP) and ribonuclease A (RNase A). 2'CMP is known as a strong inhibitor of substrates that bind to the active site of RNase A. Both reagents were prepared in 50 mM potassium acetate buffer, pH 5.5. Similarly, at varying molar ratios (2'CMP/RNase A) from 0.1 to 2, the device output exhibited titration-dependent spikes in correspondence to the molar ratio as shown in FIG. 13. ITC measurements of 2'CMP-RNase A binding at controlled temperatures of 23° C. and 35° C. with error bars from three measurements at each molar ratio were also performed. In turn, the temperature-dependent thermodynamic properties associated with this biomolecular interaction were determined from fitting the experimental data to the described model in Equation 3. The results again agreed reasonably with published data using commercial ITC instruments as shown in FIG. 14. For 2'CMP-RNase A interaction, the reasonably detectable concentration of RNase A can be as low as 2 mM. These results demonstrate the utility of this MEMS-ITC device for efficient characterization of a wide variety of biomolecular interactions.

The foregoing merely illustrates the principles of the disclosed subject matter. Various modifications and alterations to the described embodiments will be apparent to those skilled in the art in view of the inventors' teachings herein. Features of existing microelectromechanical or calorimetric systems can be seamlessly integrated into the exemplary embodiments of the disclosed subject matter or a similar system. It will thus be appreciated that those skilled in the art will be able to devise numerous systems and methods which, although not explicitly shown or described herein, embody the principles of the disclosed subject matter and are thus within its spirit and scope.

We claim:

1. A microelectromechanical systems-based calorimetric device for characterization of biomolecular interactions comprising:
   a first micromixer;
   a second micromixer;
   a thermally-isolated reaction chamber in fluid contact with the first micromixer;
   a thermally-isolated reference chamber in fluid contact with the second micromixer; and
   a thermoelectric sensor configured to measure at least one temperature metric associated with the reaction chamber and the reference chamber;
   wherein the first micromixer comprises a passive chaotic micromixer.

2. The microelectromechanical systems-based calorimetric device of claim 1, wherein the passive chaotic micromixer comprises a serpentine channel.

3. The microelectromechanical systems-based calorimetric device of claim 2, wherein the serpentine channel comprises herringbone shaped ridges.

4. The microelectromechanical systems-based calorimetric device of claim 1, further comprising a first inlet and a second inlet in fluid contact with the first micromixer.

5. The microelectromechanical systems-based calorimetric device of claim 1, wherein the reaction chamber comprises a polydimethylsiloxane microchamber.

6. The microelectromechanical systems-based calorimetric device of claim 1, wherein the reference chamber comprises a polydimethylsiloxane microchamber.

7. The microelectromechanical systems-based calorimetric device of claim 1, wherein the reaction chamber comprises a serpentine chamber.

8. The microelectromechanical systems-based calorimetric device of claim 1, wherein the reference chamber comprises a serpentine chamber.

9. The microelectromechanical systems-based calorimetric device of claim 1 further comprising a polyimide diaphragm that serves as a base for the reaction chamber.

10. The microelectromechanical systems-based calorimetric device of claim 1, wherein the thermoelectric sensor comprises a thermopile.

11. The microelectromechanical systems-based calorimetric device of claim 10, wherein the thermopile comprises an antimony-bismuth thermopile.

12. The microelectromechanical systems-based calorimetric device of claim 10, wherein a first thermopile junction is located on a first side of the reaction chamber.

13. The microelectromechanical systems-based calorimetric device of claim 12, wherein a second thermopile junction is located on the first side of the reference chamber.

14. The microelectromechanical systems-based calorimetric device of claim 1, wherein the reaction chamber is surrounded by an air cavity.

15. The microelectromechanical systems-based calorimetric device of claim 14, wherein the air cavity comprises a serpentine channel.

16. The microelectromechanical systems-based calorimetric device of claim 1, wherein the reference chamber is surrounded by an air cavity.

17. The microelectromechanical systems-based calorimetric device of claim 1, wherein the reaction chamber comprises a chamber temperature sensor.

18. The microelectromechanical systems-based calorimetric device of claim 17, wherein the reaction chamber further comprises a heater.

19. The microelectromechanical systems-based calorimetric device of claim 1, wherein the at least one temperature metric comprises a differential temperature between the reaction chamber and the reference chamber.

20. The microelectromechanical systems-based calorimetric device of claim 1, wherein the at least one temperature metric comprises a temperature of the reaction chamber and a temperature of the reference chamber.

* * * * *